United States Patent [19]
Sharp

[11] Patent Number: 5,603,334
[45] Date of Patent: Feb. 18, 1997

[54] APPARATUS FOR MEASURING AND DEVELOPING PROPRIOCEPTIVE ABILITY

[76] Inventor: Gregory M. Sharp, P.O.Box 922, Summerland, Calif. 93067

[21] Appl. No.: 280,472

[22] Filed: Jul. 25, 1994

[51] Int. Cl.⁶ ............................................. A61B 5/10
[52] U.S. Cl. ............................................. 128/779; 482/146
[58] Field of Search ........................ 128/774, 779, 128/782; 33/511, 512; 273/449; 482/96, 146

[56] References Cited

U.S. PATENT DOCUMENTS

| | | | |
|---|---|---|---|
| 3,090,226 | 5/1963 | Corti et al. | 128/782 |
| 3,712,294 | 1/1973 | Muller | 128/782 |
| 3,859,736 | 1/1975 | Hill et al. | 272/1 R |
| 4,463,946 | 8/1984 | Wallace et al. | 272/111 |
| 4,598,717 | 7/1986 | Pedotti | 128/779 |
| 4,653,748 | 3/1987 | Seel et al. | 272/96 |
| 5,112,045 | 5/1992 | Mason et al. | 482/9 |

FOREIGN PATENT DOCUMENTS 2641183  7/1990  France ..................... 128/779

*Primary Examiner*—Max Hindenburg
*Attorney, Agent, or Firm*—Michael G. Petit

[57] ABSTRACT

A device is presented for quantitatively measuring and developing proprioceptive ability. The device is also useful for rehabilitating injuries, particularly those to the lower body. The device comprises a rigid platform affixed to an inelastic, unstable rocker assembly by means of a support. In one preferred embodiment the rocker assembly rests on the floor. In another embodiment, the rocker assembly rests on the surface of a contact bed. The user stands on the platform and, by shifting his/her center of gravity with respect to the unstable rocker assembly, brings the platform into approximate balance wherein the plane of the platform is substantially parallel to the floor within certain limits. The ability of the user to keep the plane of the platform within a predetermined range of inclination with respect to the horizontal, measured as a function of time, enables quantification of the increase in proprioceptive ability. The device also provides rehabilitative and conditioning exercise.

3 Claims, 4 Drawing Sheets

APPARATUS FOR MEASURING AND DEVELOPING PROPRIOCEPTIVE ABILITY

BACKGROUND OF THE INVENTION

1. Technical Field

The invention relates to an apparatus for determining and improving proprioceptive ability.

2. Background Information

Proprioception relates to the sensation of body movements and awareness of posture, enabling the body to orient itself in space. Sensory clues associated with proprioception originate from within the body from sensory nerve terminals found in muscle joints, tendons and the inner ear which are sensitive to body position and movement. Proprioceptive ability is a learned behavior.

A device for measuring the ability of a person to balance is presented in U.S. Pat. No. 4,122,840 to Tsuchiya, et al. In the '840 patent, a device is described wherein a person to be tested steps on a pair of foot steps and a plurality of body load detectors sense the body load of the person as applied to the footsteps. An arithmetic circuit receives the body load signals and provides difference signals which are displayed so that the person being tested can observe them. That is, the person being tested "sees" body load distribution patterns on a display and adjusts his body balance as a function thereof and in response thereto. A key feature of the device set forth in the '840 patent is the use of visual cues to enable a person to develop balance. The visual cues appear on a monitor that the person being tested reacts to.

Desjardines, et al. in U.S. Pat. No. 4,850,588 describe a balancing apparatus for surfboards. The balancing apparatus generally comprises a platform, upon which a person can stand, mounted on top of a support post by means of a main universal joint. The main universal joint allows the platform to tilt or pivot about the support post. The apparatus includes means connected between the platform and the post for tilting the platform on the post about first and second axes orthogonal to and passing through the center axis of the main universal joint. Thus, the tilting means provides a side-to-side yawing motion to the surfboard on the post about the first axis and also provides a fore and aft pitching motion to the surfboard on the post about the second axis. The tilting means can be operated to simultaneously combine the yawing and pitching motions. There is, however, no means on the device to start and stop a timing device when the board is in or out of balance. Moreover, there is no means for adjusting the limits within which a board can be considered to be in balance. Thus, it is difficult to determine accurately whether or not a person's balance is improving with extended use of the apparatus. That is, the device does not provide a quantitative method for measuring proprioceptive ability.

Wallace, et al. in U.S. Pat. No. 4,463,946, the contents of which patent is incorporated herein by reference, describe a fitness evaluation apparatus for quantitatively measuring a person's physical fitness, agility and reaction time. The device measures the ability to maintain and regain balance and includes a balance beam on which the test subject stands. The apparatus includes a counter for counting the number of times balance is lost during a test cycle and a timer for timing the duration of imbalances during the test cycle. Thus, the Wallace, et al. apparatus provides a means for measuring a person's ability to balance over a test time period which includes the number of times a person went out of balance and the duration of the periods that were out of balance. The disadvantage of the Wallace, et al. device is that it employs a balance beam which enables a person to balance in only a single plane. That is, there is a single axis through a balance beam around which axis a balancing board rotates which permits only a pitching motion or a side-to-side yawing motion but not both simultaneously. The balanced board can only rotate in the plane perpendicular to the axis of the balance beam. Thus, the balancing platform does not provide a 360° dynamic plate which must be held in balance but rather only a movable beam that rotates in a single plane.

An interesting device for simulating flight and weightlessness is described in U.S. Pat. No. 3,859,736 to Hill, et al. The device, referred to as a kinesthetic control simulator, has a flat base which rests upon a support structure having a lower spherical surface for rotation. Columns support the platform above the support structure at a desired location with respect to the center of curvature of the spherical surface. A handrail is provided at approximately the elevation of the hips of the operator above the platform with a ring attached to the support structure which may be used to limit the angle of tilt. The device resembles a telephone booth mounted upon the flat surface of a section sliced from a sphere. The balance position is achieved by pneumatic or thrust means depending upon the embodiment. The device does not respond to changes in the body's center of gravity to maintain a balanced position, but rather the manipulation of pneumatic or thrusting devices are employed to maintain balance. Moreover, there is no means for quantitatively measuring the amount of time spent out of balance during a test period.

With each of the foregoing devices, there is shown to be a general lack of features which permit a person to measure their proprioceptive skills quantitatively. Mason, et al. in U.S. Pat. No. 5,112,045 describe a device for diagnosing and rehabilitating bodily injuries. The device comprises a rigid platform resting atop an elastically deformable support member much like an inner tube. The patient stands on the platform and balances or performs other exercises on the platform which require the patient to work against the instability of the support member. The performance of the exercises enables diagnosis and rehabilitation of any kind of anesthetic impairment which the patient may be experiencing. This device like the previous devices does not provide means for determining how long a portion of a test period is spent out of balance and what portion is spent in balance and therefore is not useful for quantitatively evaluating and developing proprioceptive ability.

Jain, et at. in U.S. Pat. No. 5,209,240 describes a device for registering and recording induced imbalance in a human subject. A horizontal platform is adapted for controlled linear displacement in a horizontal plane to induce imbalance. Imbalance and response can be detected and recorded by means of electric contact shoes or other means. This device differs from the previous devices in that rather than measuring a person's ability to maintain a balanced position wherein the user has complete control over the position of the device, the Jain, et at. device induces an imbalance that the user must respond to. The Jain device does not, however, provide simultaneous motion in three dimensions. The displacements of the platform are limited to a controlled displacement in a horizontal plane. That is, the plane of the platform itself. It is the sort of motion that makes one lurch and stumble about until they regain their motion, much like stepping on an escalator or the motion one experiences during an earthquake or stepping onto a treadmill belt.

In view of the foregoing devices and their limitations, there is seen to be a need for an apparatus which enables the user to balance with simultaneous motion about two perpendicular axes to bring a platform into balance and to quantitate the amount of time the board is in and out of balance during a particular test period.

SUMMARY OF THE INVENTION

The present invention provides a proprioceptive ability measurement device which enables the user to track his/her progress toward improving their balance by supplying feedback, in the form of the amount of time balanced during a session. The device enables the user to set several parameters including: a) the height of the platform above the ground, b) the range of inclination with respect to the horizontal within which the platform is considered to be balanced, c) the degree of difficulty in maintaining a state of balance; and d) the amount of time in balance and the total elapsed time the user is on the device. At the end of an exercise session, the device may provide the user with any or all of the following data: the total time the user was within a predetermined range considered as a balanced state, or the longest continuous amount of time balanced.

DESCRIPTION OF THE PREFERRED EMBODIMENTS

Figure 1:
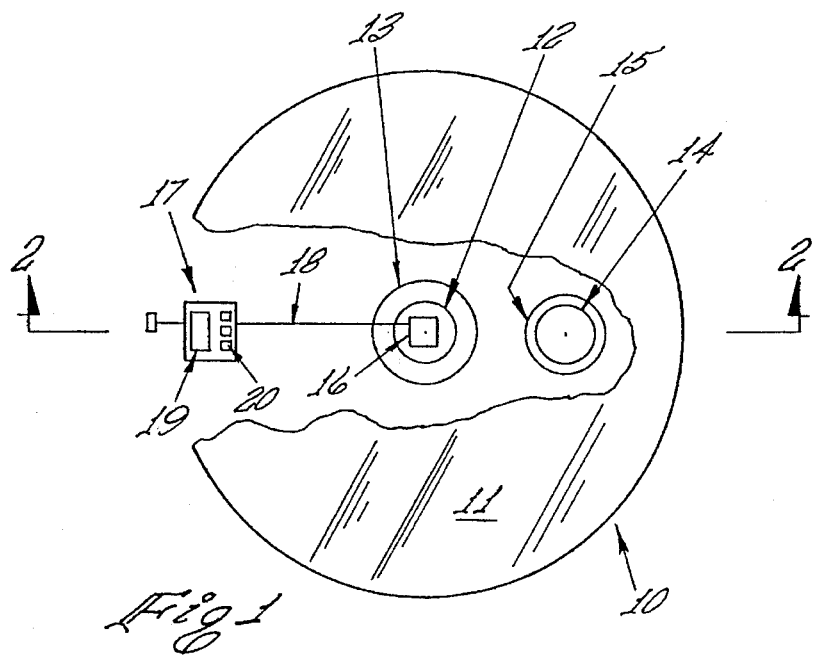
FIG. 1 is a partially cut away top view of a preferred embodiment of the apparatus of the present invention.

A particularly preferred embodiment of the device in accordance with the present invention is set forth in FIGS. 1–5. The invention is described below with reference to these figures. The apparatus of the present invention, generally indicated at the numeral 10 in FIG. 1, comprises a rigid circular platform 11 which rest atop a rigid, inelastic support 12. The support 12 has means thereon for adjustably and releasably engaging a substantially rigid, inelastic rocker assembly 13. Such adjustable, releasably engaging means may, for example, include a threaded exterior on the support 12 which matingly engages a threaded interior 31 on the rocker assembly (see FIG. 3) or a series of holes (not shown) in the support 12 which can be aligned with mating holes (not shown) in the rocker assembly 13 and pinned into position. The rocker assembly 13 preferably has a threaded exterior run 31 that matingly engages the support 12. Attached to the run 31 is a semispherical member 33 having a radius of curvature and which serves as a pivot point for the platform. The user can adjust the height of the platform 11 in relation the to floor (not shown) by screwing the rocker assembly 13 into or out of the support 12. This also provides a means for adjusting the angle that the platform is allowed to travel on an axis parallel to the floor. The higher the platform 11 is above the floor, the greater the possible angle of inclination of the platform 11 with respect to the horizontal plane.

The circular platform 11 is fitted with at least one extra support 14 to hold extra rocker assemblies 15. The user can adjust the degree of difficulty by interchanging the rocker assemblies 13 and 15. The rocker assemblies 13 and 15 differ in radius of curvature of the floor-contacting surface 32 and/or material, to provide different levels of difficulty. In general, the smaller the radius of curvature of the semispherical portion 33 (FIG. 3) of the rocker assembly 13, the greater the level of difficulty maintaining balance.

The platform 11 has a sensor 16 that determines the angle of inclination of the plane of the circular platform 11 with respect to the horizontal plane. A preferred sensor is a electro-mechanical device that will provide an electrical signal corresponding to the angle of the inclination of the platform. In a preferred embodiment, the sensor 16 comprises a pair of pendulum resistors having a range of 0°–60° (Model CP 17-0663-1 Pendulum resistor, Humphrey, Inc., San Diego, Calif.). The pendulum resistors are orthogonally mounted with respect to another on the lower or floor-facing surface of the platform 11 to measure the pitch and yaw of the platform. The electrical signal from each of the individual pendulum resistors comprising the sensor 16 are communicated to a computer 17 via a conductor 18. The computer 17 processes the sensor signals to compute whether the platform is balanced and stores and accumulates the time the user is balanced and computes other information as appropriate. The computer 17, which is preferably a microprocessor, has a display 19 and keyboard 20 that permits the user to communicate with the microprocessor. Such communication includes entering the total time that the user wishes to exercise on the device, the range in the angle of inclination the plane of the platform 11 is allowed to make with respect to the horizontal plane before the computer sends an out-of-balance signal to a balance timer 62 (FIG. 6) which turns the timer on or off. The computer 17 may also have a port that allows it to communicate with a remote device.

Figure 5:
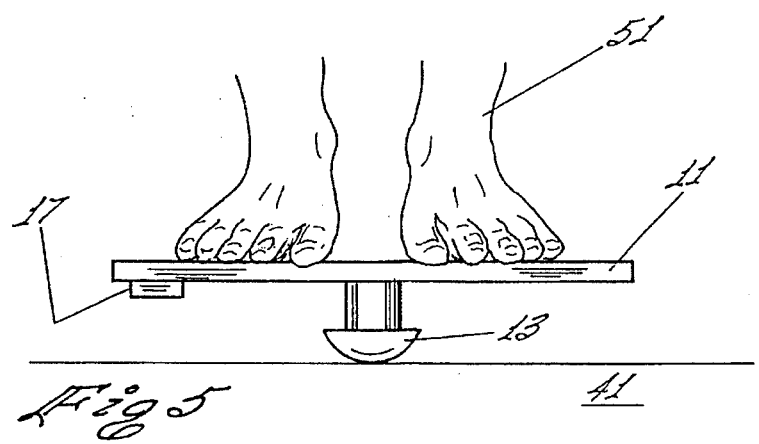
FIG. 5 is a side view of the apparatus in the balanced position.
Figure 4:
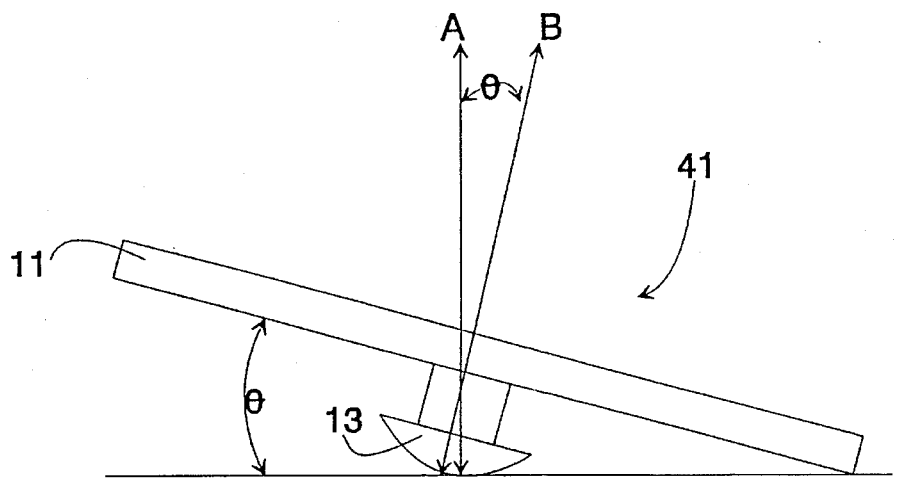
FIG. 4 is a side view of the apparatus showing the orientation of the apparatus with respect to a supporting surface.

An end-on view of the device is seen in FIG. 5. A user 51 stands on the platform 11 which is supported above the floor 41 by a rocker assembly 13. The user 51, by shifting his/her weight in response to physical sensations, brings the platform into balance. The plane of the platform 11 will intercept the horizontal plane at an angle $\Theta$ as shown in FIG. 4. When the platform is "in balance," $\Theta$ ranges between 0 and $\Phi$, where $\Phi$ is an arbitrary angle set by the user, usually between 5° and 10°. The range of the angle of inclination $\Theta$ corresponding to a balance position is $\pm\Phi$. The smaller $|\Phi|$ is, the more difficult it is to maintain the balance position. In the limit as $\Phi$ approaches 0, only a horizontal platform will define the "in balance" condition.

Figure 6:
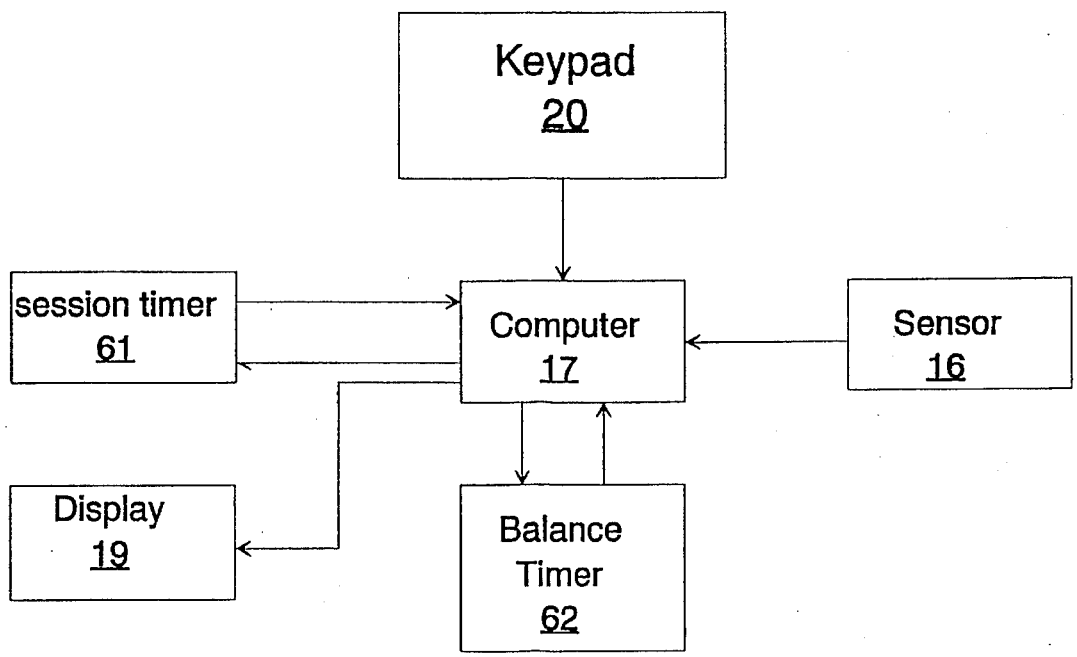
FIG. 6 is a schematic diagram of the electronic components arranged in accordance with the present invention.

When the user is about to commence a session, he will turn the apparatus on and enter the session time into the computer 17 via a keypad 20 (FIG. 6). The user will then enter a range Φ into the computer 17, either manually or through the keypad 20 and step onto the platform. When the platform is balanced so that the absolute value of the angle Θ of the platform 11 plane is less than or equal to |Φ|, the sensor 16 signals the computer 17 that the session has begun and the computer signals the session timer 61 to begin counting down. The computer 17 also causes the balance timer/accumulator 62 to begin counting. The session timer 61 continues to count until the session is over. The balance timer 62, however, only counts when the platform is in balance. The keypad 20 is preferably accessible from the top or upper surface of the platform 11 and can be used to select which timer is being displayed or both may be displayed. Batteries (not shown) may be used to provide power to the apparatus. The balance timer is provided with a reset switch or it may be reset by means of the computer via a keypad command. The display 19 is preferably mounted to be viewed from the upper surface of the platform.

Figure 7:
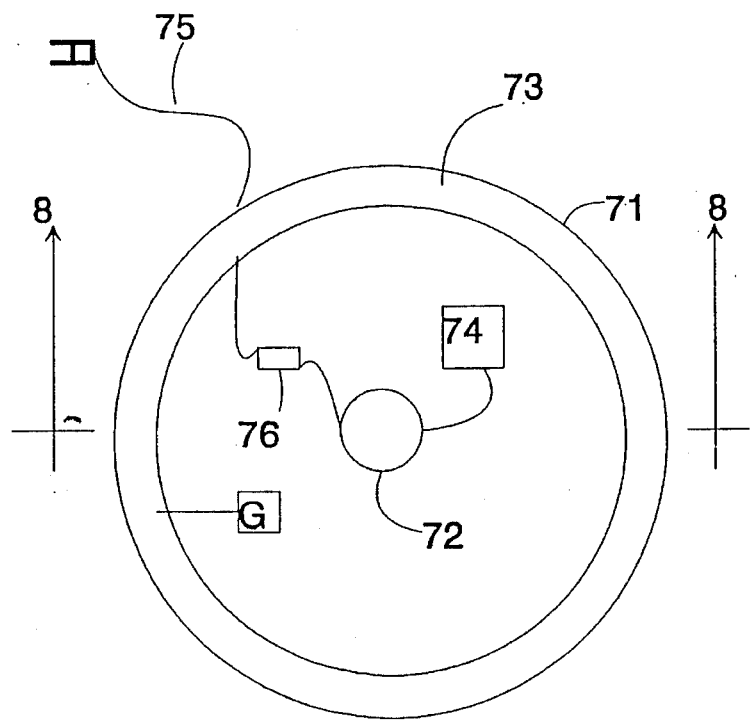
FIG. 7 is a top plan view of a second embodiment of the apparatus of the present invention employing a contact bed to generate a signal when the platform (not shown in FIG. 7) touches the contact bed.
Figure 8:
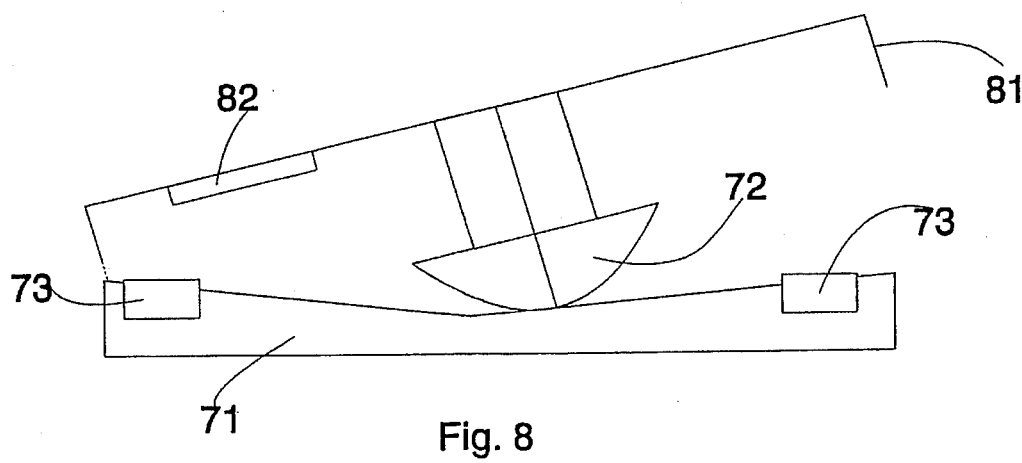
FIG. 8 is a side view of the apparatus of FIG. 7 taken along section line 8—8.

A second embodiment employing a contact bed to determine when the user is balanced is shown in FIGS. 7 and 8. A contact bed 71 is a preferably circular pad having approximately the same size as the rigid platform (removed from FIG. 7). The contact bed 71 lies on the floor (not shown), with the rocker assembly 72 resting in the center of the contact bed. Around the periphery of the contact bed 71, on the top side, is a contact ring 73 and in the center of the contact bed at the point of contact of the rocker assembly 72 with the contact bed 71 is an electrical contact point (not shown). An electrical current is supplied to each of these components by a battery pack 74. The rocker assembly is placed in the center of the contact bed. The rocker assembly is fitted with a contact point on the bottom that allows the transmission of current from the contact point on the contact bed. The contact point on the platform could also include a spring system that allows for adjustment of the rocker assembly with respect to the platform and by a transmission line, out to a circular contact ring 80 located on the bottom lip of the rigid platform. The circuit is completed when the contact ring 80 on the platform 81 (FIG. 8) contacts the contact ring 73 on the contact bed 71. The completed circuit operates a solenoid 82 to stop the accumulator timer (not shown).

Figure 9:
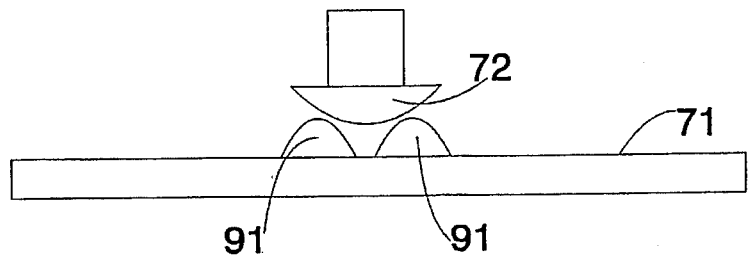
FIG. 9 is a side view of an alternative embodiment of the platform support and rocker assembly of the present invention.

The top surface of the contact bed 71 is concave as shown in FIG. 8 to keep the rigid platform centered on the contact bed. The concave surface prevents the rocker assembly 72 from "walking" uphill toward the edges of the contact bed 71. Another possible embodiment employs four mounted and electrified ball bearings 91 at the center of the contact bed, as shown in FIG. 9. The bearings 91 are positioned to accommodate the rocker assembly thereupon. As the platform (not shown) tilts, the rocker assembly 72 rotates on top of the bearings 91. The bearings conduct a current to a contact point on the rocker assembly, signaling an out-of-balance condition.

Figure 10:
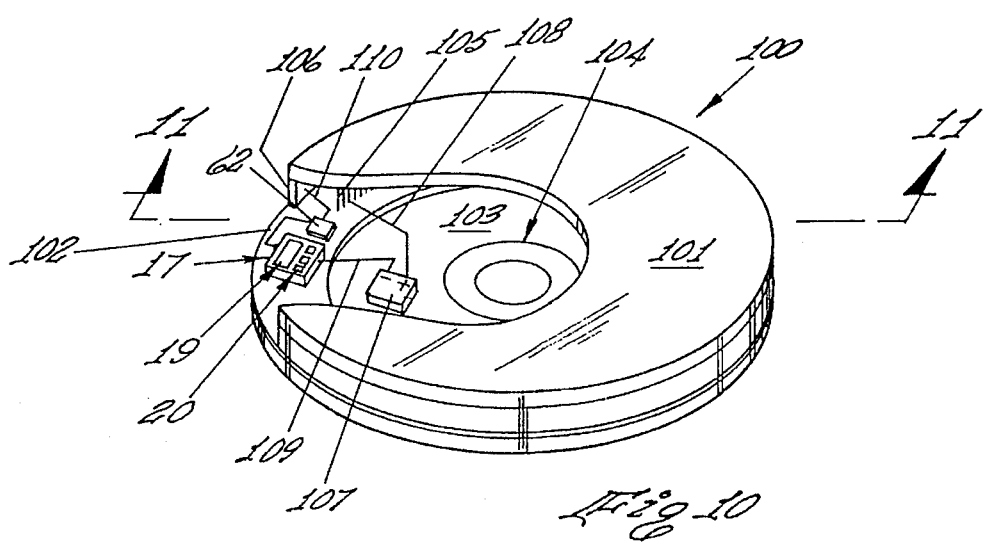
FIG. 10 is a partially cut away top view of a particularly preferred embodiment of the apparatus of the present invention.
Figure 2:
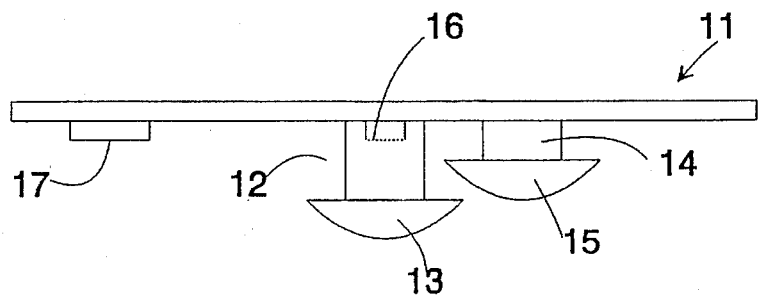
FIG. 2 is a side view of the apparatus of FIG. 1 taken along section line 2—2.
Figure 3:
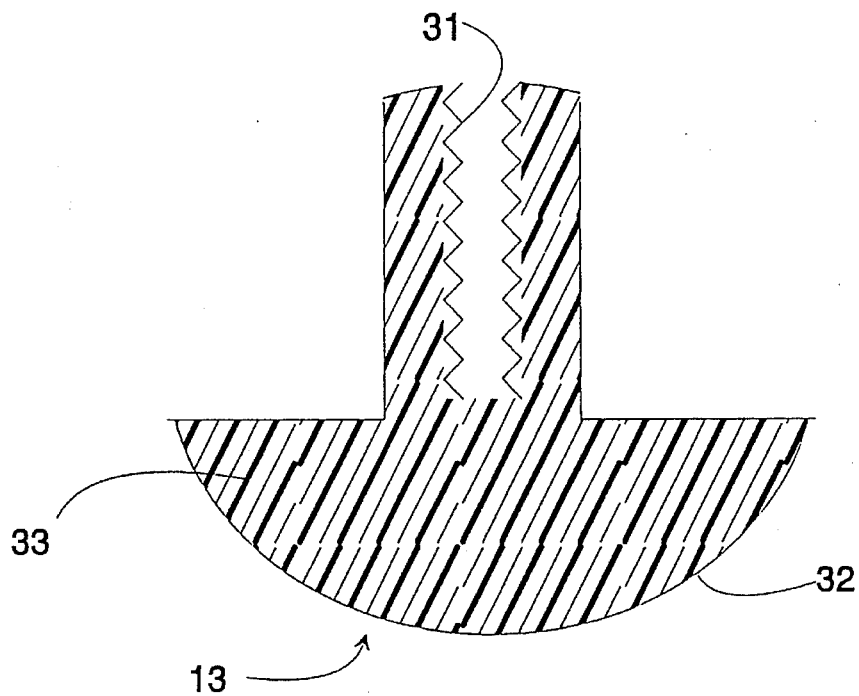
FIG. 3 is a cross-sectional view of the rocker assembly.
Figure 11:
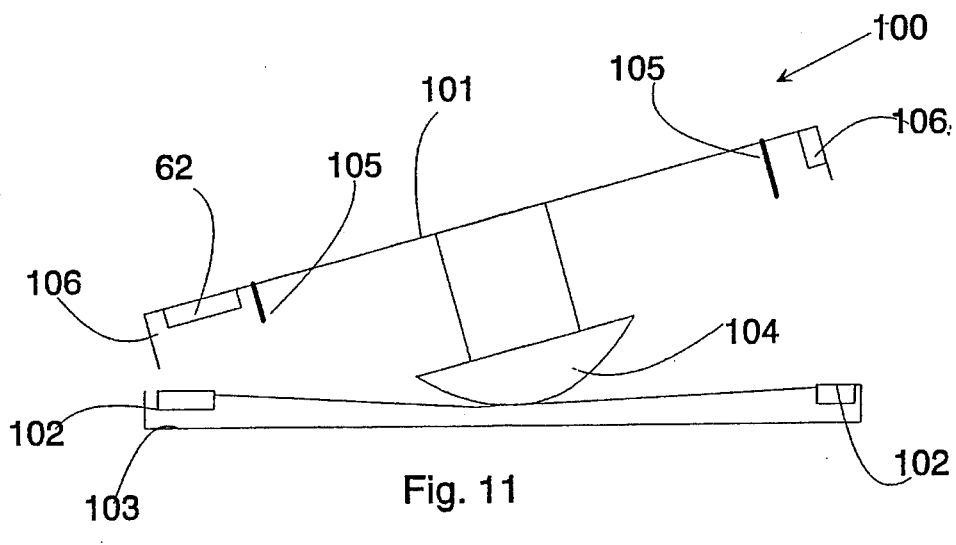
FIG. 11 is a side view of the apparatus of FIG. 10 taken along section line 11—11.

A particularly preferred embodiment of the present invention is shown in FIGS. 10 and 11. A partially cut away top view of the device is shown in FIG. 10. The device 100 comprises a platform 101 and a base 103. A conductive strip 102 encircles the upper surface of the base 103. The width of the strip is greater than the spacing between a conductive circular outer flange 106 which encircles the perimeter of the platform 101 and a concentric ring of conductive interconnected whiskers 105 located axially to the circular outer flange 106. The conductive "whiskers" are flexible and may be die cut into a portion of a strip of conductive material to resemble a comb. The "whiskers," which are similar to the teeth of a comb, are in electrical communication with one another. The "whiskers" protrude downward toward the base 103 from the bottom surface of the platform 101. One terminal of a battery 107 applies voltage to the conductive ring of interconnected whiskers 105 by means of a conductor 108. The other terminal of the battery 107 is connected to the computer 17. When at least a portion of the flange 106 and the ring of whiskers 105 make simultaneous contact with the conductive strip 102, the battery is connected across the computer by means of conductor 110. The resultant application of voltage to the computer signals the timer/accumulator 62 that the platform is "out of balance," thereby switching off the timer. The timer counts only when the circular conductive flange 106 and the ring of conductive whiskers 105 are not in electrical communication by means of simultaneous contact with the conductive strip 102 on the base 103.

In summary, the proprioceptive ability measurement device comprises a sensor fixed to a rigid platform supported above the floor in such a way that the plane of the platform can tilt with respect to the horizontal plane in all directions. The sensor signals measure the angle of inclination of the platform about two orthogonal axes and transmits the inclination to a computer. The computer compares the inclination with ΔΘ to determine whether the platform is in a balanced or an out-of-balance position and stops and starts a balance timer, as appropriate. The user sets a length of time he/she wishes to engage in the exercise (session time) and the adjusts the degree of difficulty by adjusting any of the following variables; allowed angle of movement, and the degree of difficulty of maintaining balance. The user then stands on the platform and, by shifting his/her center of gravity, brings the platform into balance thereby starting a time-in-balance timer. When the platform is out of balance, the time-in balance timer is stopped in response to a signal from the computer. A separate session timer counts down from the selected session time to 0. During the time the user is able to stay within the angular range tolerances set prior to the start of the session, the time-in-balance timer acts as an accumulator and stores the amount of time the user is successful in maintaining his/her balance. At the end of the session, a display will tell the user how long he/she was able to keep the platform balanced. The display could also tell the user the longest sustained period of balance, the number of times the user was out of balance, and/or the percentage of session time the user was in or out of balance.

While the foregoing preferred embodiments of the invention have been described and shown, it is understood that alternatives and modifications such as those suggested and other, may be made thereto and fall within the scope of the invention. For example, simple mercury switches comprising a drop of mercury which can roll in a sealed container having paired electrical contacts can be employed for an angular sensor. When the mercury drop rolls under gravity to one end of the container, it closes a circuit to indicate an in-balance or out-of-balance condition. A universal joint may be used instead of the rocker assembly to support the platform and position sensors above the floor. It is, therefore, intended to cover in the appended claims all such changes and modifications that are within the scope of this invention.

What I claim is:

1. An apparatus for measuring and developing proprioceptive ability comprising:

a) a rocker assembly comprising a rigid hemispherical member having a flat upper surface and a radius of curvature and an inelastic support post having a free end and a fixed end rigidly affixed to said flat surface;

b) a platform comprising a circular planar sheet having a lower surface and a top surface dimensioned to accommodate the feet of a user; said platform having an inelastic support integral therewith and mounted axially thereon to project from said lower surface, said inelastic support having a free end adapted to releasably engage said free end of said support post;

c) an inclination sensing means affixed to said platform, said sensing means being operable for measuring the pitch and yaw of the plane of said platform with respect to a horizontal plane and generating a signal responsive to the inclination of said platform when the angle of inclination of said platform moves into or out of a pre-set angular range;

d) a computer means in communication with said inclination sensing means, said computer means being operable for receiving a signal from said sensing means;

e) a session timer in communication with said computer means said session timer being operable for measuring the time elapsed during a session of use;

f) a balance timer in communication with said computer means;

and wherein said computer means is operable for controlling said balance timer to indicate the portion of said elapsed time during a session of use said platform is horizontal within a pre-set range and wherein said portion of the elapsed time provides a measure of proprioceptive ability.

2. A method of improving proprioceptive ability of a person comprising the steps of a) presenting an apparatus for measuring proprioceptive ability in accordance with claim 1;

b) selecting a degree of difficulty commensurate with the person's current proprioceptive ability by selecting a rocker assembly having an appropriate radius of curvature;

c) setting the computer to adjust tolerance for the pitch and yaw of the platform and the session timer;

d) standing the person on the platform; and e) measuring the percentage of the session time the platform is in balance; and f) repeating steps a–e until the said percentage of the session time the platform is in balance increases.

3. The apparatus according to claim 1 comprising a plurality of rocker assemblies wherein each one of said plurality of rocker assemblies has a different radius of curvature.

* * * * *